United States Patent
Osei-Kumi

(10) Patent No.: US 10,925,910 B2
(45) Date of Patent: Feb. 23, 2021

(54) TOPICAL COMPOSITION CONTAINING PAPAYA SEED FOR TREATING INFLAMMATORY SKIN CONDITIONS

(71) Applicant: Emmanuel Osei-Kumi, Houston, TX (US)

(72) Inventor: Emmanuel Osei-Kumi, Houston, TX (US)

( * ) Notice: Subject to any disclaimer, the term of this patent is extended or adjusted under 35 U.S.C. 154(b) by 553 days.

(21) Appl. No.: 14/930,192

(22) Filed: Nov. 2, 2015

(65) Prior Publication Data

US 2017/0119832 A1    May 4, 2017

(51) Int. Cl.
| | |
|---|---|
| *A61K 36/185* | (2006.01) |
| *A61K 47/44* | (2017.01) |
| *A61K 9/00* | (2006.01) |
| *A61K 47/06* | (2006.01) |
| *A61K 36/67* | (2006.01) |

(52) U.S. Cl.
CPC .......... *A61K 36/185* (2013.01); *A61K 9/0014* (2013.01); *A61K 36/67* (2013.01); *A61K 47/06* (2013.01); *A61K 47/44* (2013.01)

(58) Field of Classification Search
CPC ........ A61K 36/67; A61K 47/06; A61K 47/44; A61K 36/185
See application file for complete search history.

(56) References Cited

FOREIGN PATENT DOCUMENTS

| BR | 200104692 A | * | 8/2003 |
|---|---|---|---|
| CN | 104256540 A | * | 1/2015 |

OTHER PUBLICATIONS

Morton, J. "Papaya" from : Fruits of warm climates. Julia F. Morton, Miami, FL. 1987. p. 336-346. Retrieved from the internet on: Jul. 19, 2018. Retrieved from URL: <https://web.archive.org/web/20001210024100/https://www.hort.purdue.edu/newcrop/morton/papaya_ars.html>. (Year: 1987).*
Pawleyn, C. "Avocado-Papaya Salad with Papaya Seed Dressing" from Big Small Plates. Berkeley, CA 2006. p. 116. (Year: 2006).*
Page, L. "Linda Page's Healthy Healing: A Guide to Self Healing for Everyone, 11th Ed." pp. 69, 73. (Year: 2002).*
Briones, J. "Raw Vegan Papaya Seed & Coconut oil facial" from Sweet Simple Vegan. Posting Date: Oct. 14, 2014. [Retreived from the Internet on: Sep. 24, 2020]. Retrieved from: <URL: ttps://sweetsimplevegan.com/2014/10/raw-vegan-papaya-seed-coconut-oil-facial/>. 6 pages. (Year: 2014).*
Sampath, P. "Black pepper—more healthy benefits than you know!". Internet posting date: Aug. 7, 2013. [Retrieved on: Sep. 25, 2020]. Retrieved from: <URL: https://web.archive.org/web/20131114023236/https://www.dnaindia.com/health/report-black-pepper-more-health-benefits-than-you-know>. 9 pages. (Year: 2013).*
"Keeper of the Home". Homemade Cocoa Body Scrub and Body Butter. Web Posting Date: Oct. 23, 2012. [Retrieved from the Internet on: Sep. 25, 2020]. Retrieved from: <URL: https://keeperofthehome.org/homemade-cocoa-body-scrub-and-body-butter/>. 17 pages. (Year: 2012).*
Poucher's Perfumes, Cosmetics and Soaps, 10th Ed. Butler, H. Ed. eBook. p. 286. (Year: 2000).*
Dayal, R. "Premature Graying" from "Natural Beauty Secrets from India". Tate Publishing: Oklahoma, p. 13. (Year: 2008).*

* cited by examiner

*Primary Examiner* — Amy L Clark

(74) *Attorney, Agent, or Firm* — Delphine James

(57) ABSTRACT

A novel treatment for topical inflammatory conditions such as acne, eczema, shingles, insect bites, and hives is provided, consisting of the application of a herbal cream or ointment which incorporates grounded PawPaw Seeds in a granular form. The cream preferably contains one or more thickeners, a bio-adhesive agent such as petroleum jelly such that the cream can stick to the area to be treated.

10 Claims, 2 Drawing Sheets

FIGURE 1

| Year | Male | Female | Age Range | Results |
|------|------|--------|-----------|---------|
| 2007 | 10 | - | Between 20-30 | Cured within 3-7 days |
| 2007 | - | 10 | Between 40-60 | Cured within 4-7 days |
| 2008 | 6 | 20 | Between 40-60 | Cured within 3-7 days |
| 2009 | 15 | 10 | Between 40-60 | Cured in 3 days |
| 2010 | 10 | 20 | Between 20-60 | Cured in 3 days |
| 2011 | 10 | 15 | Between 30-60 | Cured in 3 days |
| 2012 | 20 | 15 | Between 60-70 | Cured in 5 days |
| 2013 | 20 | 30 | Between 50-70 | Cured in 5 days |

FIGURE 2

Formulation

- Paw Paw Seeds    95%   2 grams
- Black Pepper     5%    .1 grams
- Adhesive Agent   6-7 teaspoons Petroleum Jelly Shea Butter

TOPICAL COMPOSITION CONTAINING PAPAYA SEED FOR TREATING INFLAMMATORY SKIN CONDITIONS

CROSS-REFERENCE TO RELATED APPLICATIONS

This application claims the benefit of U.S. Provisional Application No. 62/073,988, filed on Nov. 1, 2014. The entire disclosure of the prior application is hereby incorporated by reference in its entirety.

BACKGROUND

The present invention relates to the treatment of inflammatory conditions, and more particularly to a formulation or composition for topical administration that is designed to treat itching due to inflammatory conditions such as acne, eczema, shingles, psoriasis, insect bites, and hives.

SUMMARY OF THE INVENTION

Generally speaking, in accordance with the invention, it has been discovered that topical inflammatory conditions more specifically shingles, can be effectively treated with Paw Paw Seeds Ointment ("PAWPAW") in order to lessen or eliminate inflammation. In the inventive formulation, paw paw seeds in a granulized or micro-granulized form, and preferably combined with one or more adhesive agents in order to form a pharmaceutical cream or ointment.

The above and other objects, features and advantages of the present invention should become even more readily apparent to those skilled in the art upon a read in of the following detailed description in conjunction with the drawings wherein there is shown and described illustrative embodiments of the invention.

BRIEF DESCRIPTION OF DRAWINGS

This invention is described by appended claims in relation to description of a preferred embodiment with reference to the following drawings which are described briefly as follows:

FIG. 1 illustrates a table that shows results of trials of the ointment.

FIG. 2 illustrates the formulation

DETAILED DESCRIPTION OF THE INVENTION

The present invention provides a novel treatment for topical inflammatory conditions such as acne, eczema, shingles, psoriasis, insect bites, and hives. The treatment consists of the application of a cream or ointment which incorporates granulized pawpaw seeds. The cream or ointment is applied to the effected area on the skin.

The aims of treatment are to limit the severity and duration of pain, shorten the duration of a shingles episode, and reduce complications. However, a study on untreated herpes zoster shows that, once the rash has cleared, postherpetic neuralogia is very rare in people under 50 and wears off in time; in older people the pain wore off more slowly, but even in people over 70, 85% were pain free a year after their shingles outbreak.

The inventive cream is prepared by making a suspension of ground pawpaw seeds within an adhesive agent by mixing the two together. Papaya or Paw Paw is the fruit of the plant *Carica papaya*, the sole species in the genus *Carica* of the plant family Caricaceae. The formulation further comprises adding granulized black pepper to the mixture. Black pepper (*Piper nigrum*) is a flowering vine in the family Piperaceae, cultivated for its fruit, which is usually dried and used as a spice and seasoning. The fruit, known as a peppercorn when dried, is approximately 5 millimetres (0.20 in) in diameter, dark red when fully mature, and, like all drupes, contains a single seed. Peppercorns, and the ground pepper derived from them, may be described simply as pepper, or more precisely as black pepper (cooked and dried unripe fruit).

The granulized Paw Paw Seeds of the inventive formulation come from a fruit that is a small yellowish-green to brown berry, 2-6 in long and 1-3 inches broad weighting from 0.7-18 oz. The fruit further contains brown seeds ½ to an 1 inch in diameter embedded in a soft edible fruit pulp. The fruit is preferably grown from the species of pawpaw from Ghana. The main agent in the composition of the present invention comprises granules of seeds from the pawpaw fruit. It is important that the pawpaw seeds are granulized to the point so that it makes intimate contact with the skin. The particle size should be between 0.10 to 10 microns in size. The weight percentage of the granulized seeds in the composition is between 1% and 2%.

An adhesive agent is used to act as a thickener that holds the granules together when placed upon the skin. Petroleum Jelly is a white petrolatum, soft paraffin semi-solid mixture of hydrocarbons. Petroleum Jelly has a melting point of a few degrees of human body temperature and is moisture or water repellant. It is colorless or has a pale yellow color, translucent and devoid of taste and smell when pure. When placed on skin it prevents moisture loss thereby preventing chapping of the skin. The weight percentage of the adhesive agent in the composition is between 1% and 2%.

An alternative adhesive agent is shea butter. Shea an off-white or ivory-colored fat extracted from the nut of the African shea tree (*Vitellaria paradoxes*). It is widely used in cosmetics as a moisturizer, salve or lotion. Shea butter is edible and is used in food preparation in Africa Another alternative adhesive agent is Cocoa butter, also called the obroma oil, is a pale-yellow, edible vegetable fat extracted from the cocoa bean. It is used to make chocolate, as well as some ointments, toiletries, and pharmaceuticals. Cocoa butter has a cocoa flavor and aroma.

The inventive cream composition further comprises granules of black pepper which come from the species. The weight percentage of the black pepper in the composition is between 1% and 2%.

Nevertheless, as shown in FIG. 1 one trial studying patients older than 50 years of age with localized herpes zoster suggested that administration of the inventive composition improved healing time to 3 to 5 days and quality of life.

What is claimed is:

1. A composition for the treatment of a topical inflammatory disease of the skin in the form of a topical cream suspension comprising an adhesive agent in an amount of between 1-2 wt %, wherein the adhesive agent is petroleum jelly, cocoa butter or shea butter, granulized papaya seeds with a particle size between 0.1-10 microns in an amount of between 1-2 wt %, and granulated black pepper in an amount of between 1-2 wt %.

2. The composition of claim 1, wherein the adhesive agent is petroleum jelly.

3. The composition of claim 1, wherein the adhesive agent is shea butter.

4. The composition of claim 1, wherein the adhesive agent is cocoa butter.

5. A composition for the treatment of a topical inflammatory disease of the skin in the form of a topical cream suspension comprising effective amounts of an adhesive agent, granulized papaya seeds with a particle size between 0.1-10 microns, and granulated black pepper.

6. The composition of claim 5, wherein the adhesive agent is cocoa butter.

7. The composition of claim 5, wherein the adhesive agent is petroleum jelly.

8. The composition of claim 5, wherein the adhesive agent is shea butter.

9. A method of making the composition of claim 5, comprising:
   granulating papaya seeds to a size of 0.01-10 microns;
   combining the granulated papaya seeds with an adhesive agent to provide a suspension; and
   adding granulized ground pepper to the suspension.

10. A composition for the treatment of a topical inflammatory disease of the skin in the form of a topical cream suspension comprising an adhesive agent in an amount of between 6-7 teaspoons, granulized papaya seeds with a particle size between 0.1-10 microns in an amount of 2 grams, and granulated black pepper in an amount of 0.1 gram.

* * * * *